United States Patent [19]

Bowen et al.

[11] Patent Number: 4,652,125
[45] Date of Patent: Mar. 24, 1987

[54] FILM INSPECTION SYSTEM

[75] Inventors: Howard Bowen, Northbrook; David Henderson, Mundelein; Carl Olson, Vernon Hills, all of Ill.

[73] Assignee: Research Technology International, Lincolnwood, Ill.

[21] Appl. No.: 692,680

[22] Filed: Jan. 18, 1985

[51] Int. Cl.[4] ............................................. G01N 21/89
[52] U.S. Cl. .................... 356/237; 250/562; 250/572; 356/430
[58] Field of Search ................ 356/237, 430; 250/562, 250/572; 73/157

[56] References Cited

U.S. PATENT DOCUMENTS

| | | | |
|---|---|---|---|
| 3,759,095 | 9/1973 | Short, Jr. et al. | 73/157 |
| 3,856,414 | 12/1974 | Menary | 356/237 X |
| 3,935,468 | 1/1976 | Bowen et al. | 356/237 X |
| 3,952,591 | 4/1976 | Manske et al. | 73/157 |
| 4,166,700 | 9/1979 | Bowen et al. | 356/381 |
| 4,264,825 | 4/1981 | Bowen | 250/560 |
| 4,276,547 | 6/1981 | Bowen et al. | 340/675 |

Primary Examiner—Davis L. Willis
Assistant Examiner—Matthew W. Koren
Attorney, Agent, or Firm—Hill, Van Santen, Steadman & Simpson

[57] ABSTRACT

A motion picture film flaw detection system wherein a single inspection location is employed at which sound track side edge defects, sprocket hole side edge deflects, thickness variations, and defective sprocket holes are analyzed by optical sensors so that no physical contact on the film by feeler arms or the like occurs. Film wear such as by scratching and rubbing is reduced since minimal contact occurs with a surface of the film as it travels through the system. The sprocket holes are analyzed by optics which provide a real image on a projection plane at which location excessive elongation of the sprocket holes is checked. Detection circuits are provided connecting to the optical sensors which derive a reference which automatically tracks averaged or weighted overall signal levels for comparison to signal variations caused by film thickness changes or film flaws. Accordingly, variations in optical system performance are automatically compensated for.

10 Claims, 16 Drawing Figures

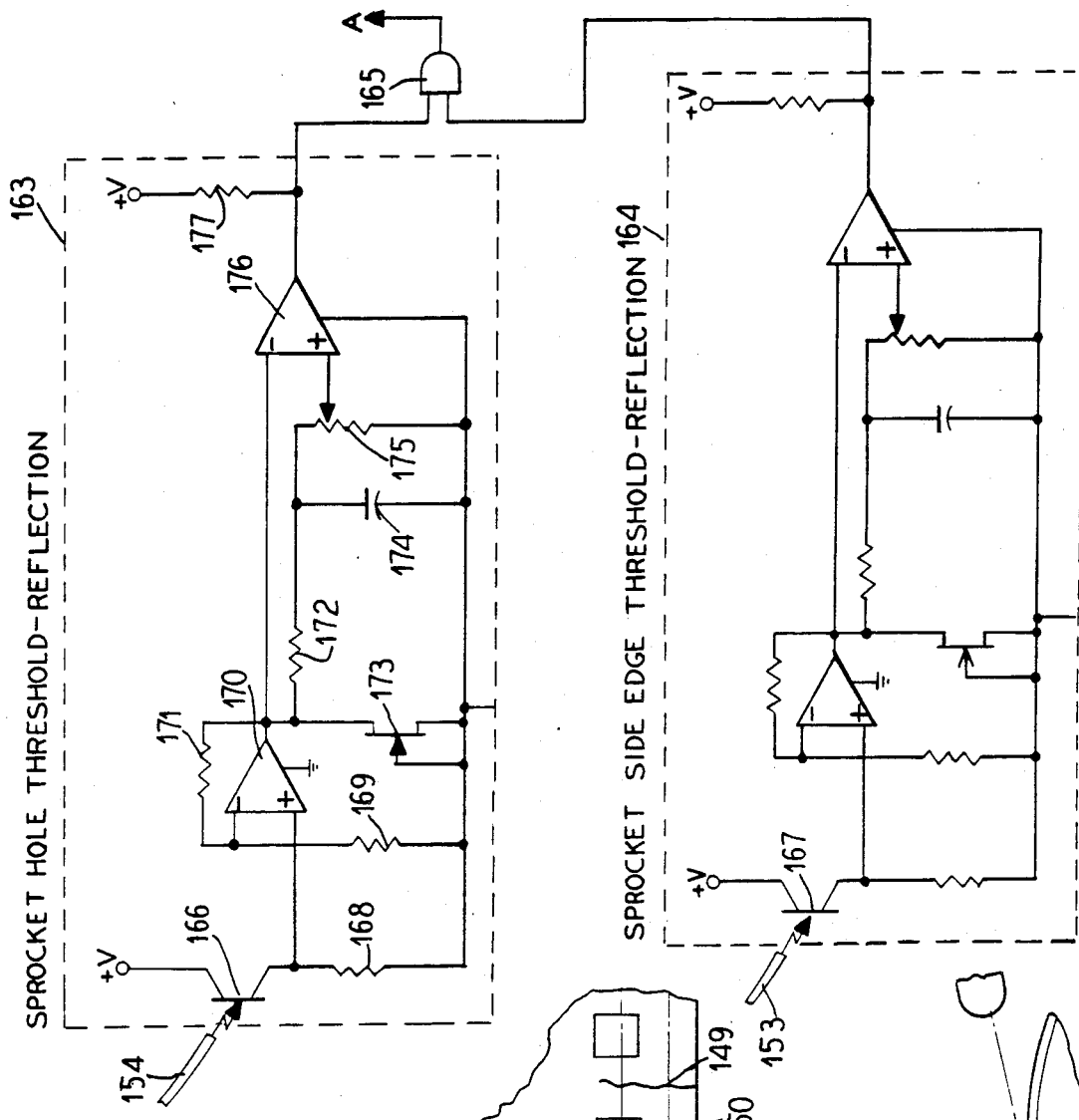
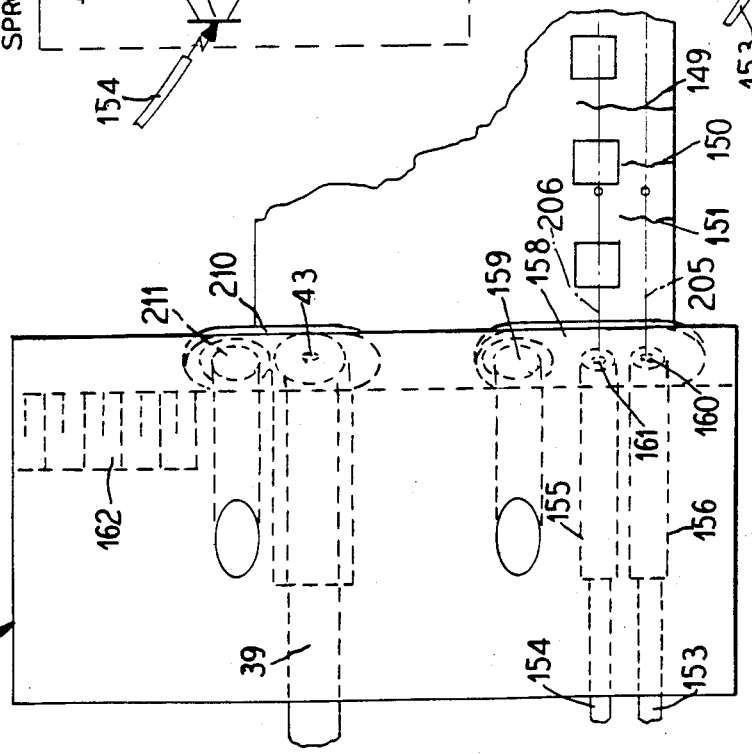
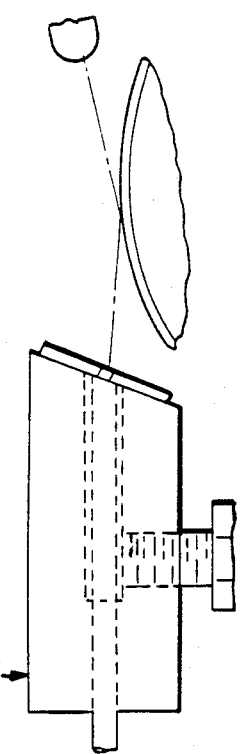

FILM INSPECTION SYSTEM

BACKGROUND OF THE INVENTION

In previous film strip inspection systems, typically for 16 mm film and which are occasionally adaptable to 8 mm or 35 mm motion picture film, various techniques have been proposed for sensing defective sprocket holes, improper thickness variations in the film such as produced by improper splicing techniques, and cracks or cuts in edges of the film.

For example, in U.S. Pat. No. 3,759,095, feelers are provided such as sapphire beads or the like attached to spring arms. The feelers ride along the surface of the film and capacitance changes are measured as a result of a movement of the feeler arm. Additionally, a spring mounted roller in contact with the film can sense for thickness changes which are translated into capacitance changes. Another feeler system is disclosed in U.S. Pat. No. 3,935,468 wherein the feeler is attached to a light blocking "flag" wherein movements of the feeler arm are translated into varying amounts of light received.

U.S. Pat. No. 4,166,700 discloses the use of a beam of light directed tangent to a surface of the film at a roller wherein thickness variations of the film are sensing as changing variations in light intensity received. In this same unit, it is also necessary to provide feeler arms which ride along edges of the film to sense for cracks or cuts and also sprocket hole defects.

U.S. Pat. No. 4,264,825 is a system for determining an abnormal length of a film splice and employs two light beams spaced at a predetermined distance, a thickness variation in the film changing the amount of light received by blocking out additional light. The system disclosed only measures for abnormal splice length.

Finally, U.S. Pat. No. 4,276,547 discloses the use of three separate feeler systems which ride on a surface of the film for respectively sensing cuts at a sound track edge of the film, abnormal length sprocket holes, and abnormal film thickness variations. Capacitance phase change sensing is employed with each of the above-identified feeler arms.

In the prior art discussed above and other similar systems in this field, in a film inspection system which analyzes not only the thickness but also edge cuts and sprocket hole damage, at least one feeler system is employed and/or with at least two separate sensing locations. Thus, when running a motion picture film through the film inspection station, the station can impart some wear to the film in view of the contact of feeler arms onto a surface of the film. Also, the plurality of stations involved increases complexity of the mechanical arrangement and increases the difficulty of threading the motion picture film into and through the film inspection station.

Also, in the prior art systems, such systems can be unduly sensitive and require frequent alignment as a result of dirt, dust, or other contaminants occurring on feeler arms, light sources, light receivers, and other related contaminations or parameter variations resulting in signal variations.

Also, in such prior art systems, it can occur that sprocket holes are not reliably inspected for defects because of insensitivity due to creases, dirt, and edge lettering on the sprocket hole edge of the film.

Thus, in the prior art systems, a number of variables such as light intensity, film reflectivity, light transmission of optics, sensitivity of photocells, dirt on the lens, a whitening of a black contrasted area can all result in varying signal levels which make it difficult to reliably detect defects given the passage of time and use of the film inspection station.

A variety of types of film must be accommodated such as white, black, shiny, and colored film. Also, sensing for an absence of material, such as in the case of a sprocket hole, thus has caused problems in prior art systems.

Additionally, in prior art systems static charges which accumulate at the film inspection station have been known to affect detection circuitry and thus result in failures or inaccurate defect or flaw detection.

SUMMARY OF THE INVENTION

It is an object of the invention to provide a film inspection system which will increase motion picture film wear to a minimal extent as a result of running the film through the detection system.

It is another object of the invention to provide a film inspection system which does not rely upon feeler arms or rollers at any point in the system for detecting flaws and thus increasing film wear.

It is a further object of the invention to guide the film through the film inspection system with minimum contact with film guide rollers and at an inspection region.

It is a further object of the invention to provide an improved system for detecting flaws in sprocket holes and particularly undesired longitudinal extension of socket holes in a direction of film travel.

It is another object of the invention to provide an inspection system for motion picture film which is designed to be insensitive to variations in light intensity, film reflectivity such as through dirt or dust, light transmission of optics, sensitivity of photocells, and other system variations resulting in sensed signal variations not due to defects.

It is a further object of the invention to detect film flaws and particularly sprocket hole flaws and defects given a variety of film colors such as may occur at film leaders or splices of different colors.

It is another object of the invention to provide a simplified film inspection station which employs a single roller at the point of film inspection and wherein a variety of film inspection techniques are employed at a same inspection region.

It is another object of the invention to provide a film inspection system for motion picture film which measures a variety of parameters of the film simultaneously to provide a thorough analysis of film quality.

It is another object of the invention to provide a film inspection system which operates without erroneous readings at initial start-up as the film is forced to run through the system after initial threading.

It is a further object of the invention to provide a simple threading system for engaging and running the film through the inspection station at start-up.

It is another object of the invention to simplify overall system adjustment and mechanics.

It is a further object of the invention to prevent static electricity charges from affecting sensing and defect determination electronics.

It is another object of the invention to count splices and to have signals available to permit the determination of film direction of travel.

It is an object of the invention to employ a "real imaging" or "microscopic" technique of film inspection analysis.

It is another object of the invention to improve a system for measuring direct beam light variations resulting from film defects.

It is a further object of the invention to detect splices which do not have sprocket holes.

It is another object of the invention to improve reflected light sensing indicative of film defects.

It is another object of the invention to be able to prevent the output of signals in response to detection of short edge cuts between sprocket holes which do not constitute serious defects.

According to the invention, a single main inspection roller is provided over which the film is guided in a curved path. At substantially a same inspection region of the film, a plurality of defect detection systems are employed so as to sense defects and thickness variations thereat. To analyze sprocket hole defects and particularly longitudinal extensions thereof along a running direction of the film, a so-called "microscope" system is employed wherein a real image of the sprocket holes is projected for analysis by spaced photodiodes. Also at the same location, edge cuts at a sound track portion of the film are analyzed through light reflection. Thickness variations at a central portion of the film are detected through a so-called "shadow graph" technique wherein a narrow slit is defined and a reduction or absence of light is detected as the slit narrows or closes. Additionally, at the same location a "shadow graph" sensing system is also employed for detecting edge cuts adjacent a sprocket hole side edge of the film.

In the microscope arrangement, diffuse light is employed. Additionally, the "pin hole" camera effect is employed in sensing for sound track edge defects and sprocket hole edge side defects.

The sensing electronics is adapted to provide a "floating reference" which automatically tracks so as to automatically adapt to system parameter changes such as dirt on the lens, different photo diode sensitivities, different optical path sensitivities, variations in film color, etc.

An improved system is provided according to the invention for analyzing edge cuts between the edge of the film and the sprocket holes.

Additionally, a splice counting system is provided in the system electronics.

The film guidance elements are designed so as to cause minimum wear on the film and a minimum contact with the film at the point of inspection. No flat rollers contact the film throughout its travel through the system. Additionally, film threading is simplified according to the invention, and detection of film defects at a start-up of the system is improved.

Also according to the invention, the definition of what constitutes a defective sprocket hole can be easily set according to the invention.

BRIEF DESCRIPTION OF THE DRAWINGS

FIGS. 11A and 11B are top and end views, respectively of an optical system of the invention for analyzing cuts at a sprocket hole edge side of the film; and FIG. 12 is a schematic illustration of an electronic sensing circuit for use with the optical system shown in FIGS. 11A and 11B.

DESCRIPTION OF THE PREFERRED EMBODIMENTS

Figure 1A:
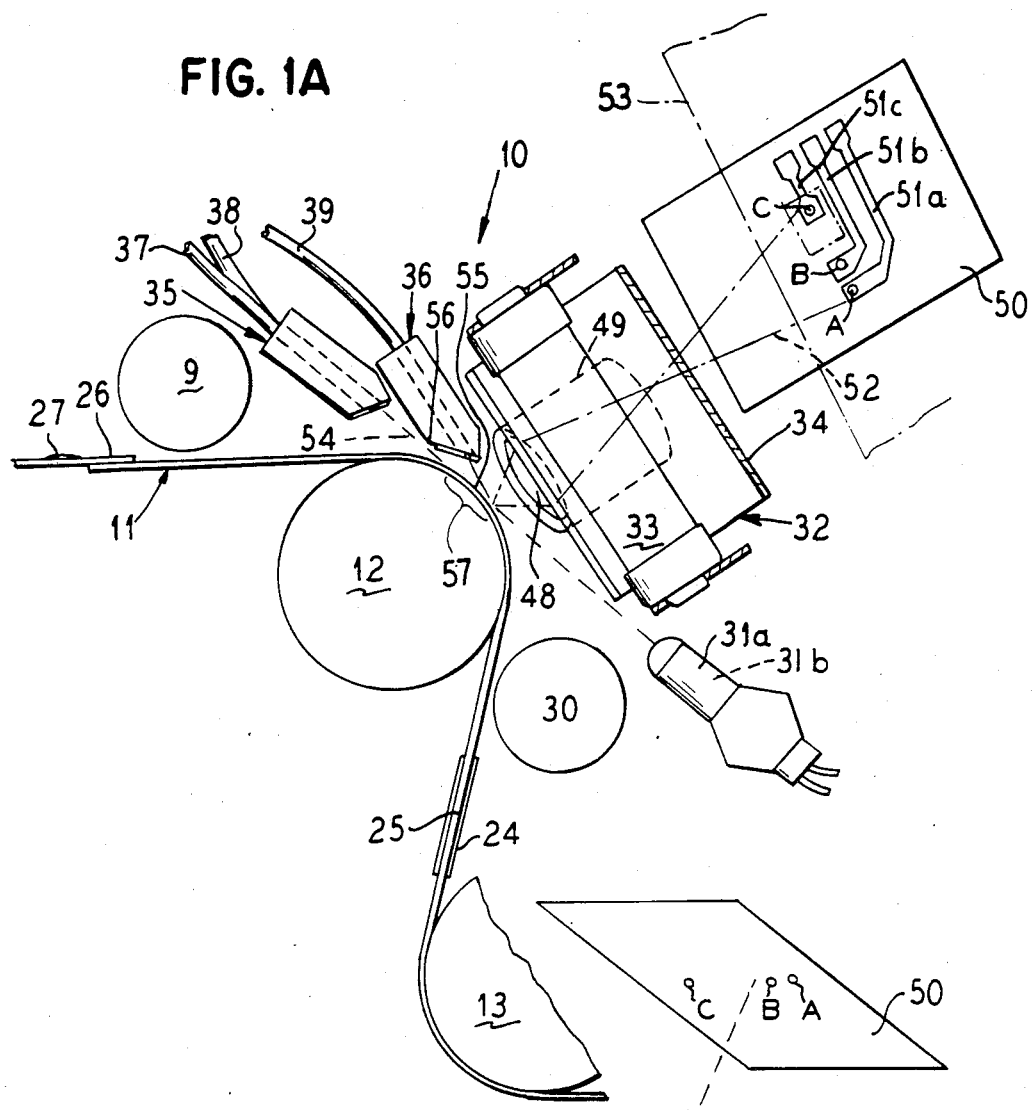
FIG. 1A is a simplified view from the side of a film inspection station in the film inspection system of the invention.
Figure 1B:
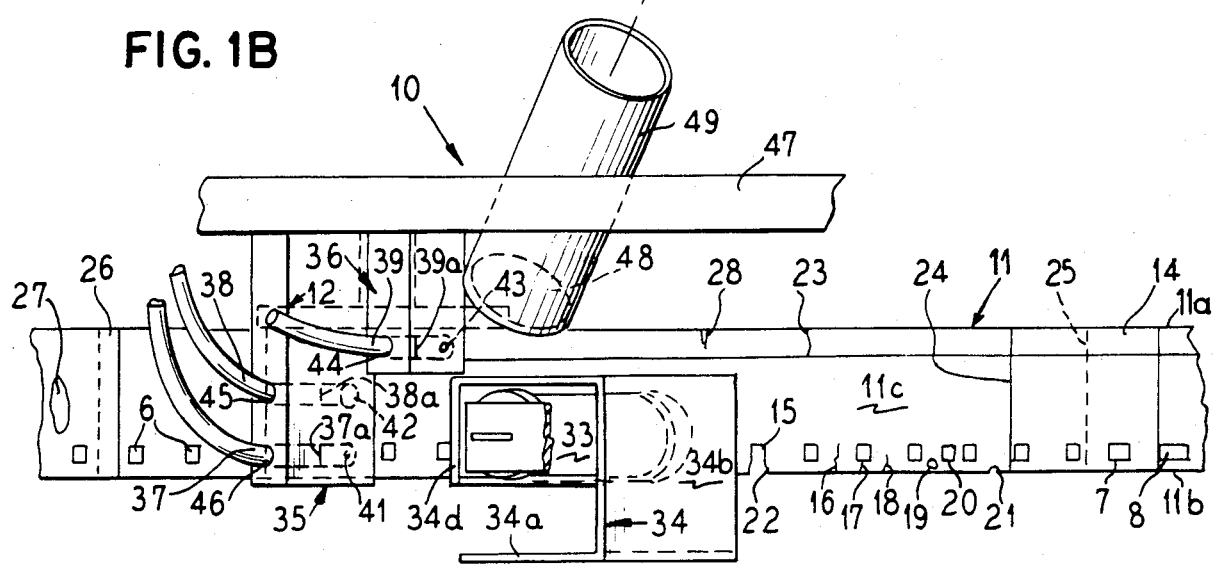
FIG. 1B is a simplified top view of the film inspection station generally illustrated in FIG. 1A.

A mechanical arrangement of the film inspection station is generally illustrated at 10 in FIGS. 1A and 1B in simplified fashion for clarity. As illustrated in FIG. 1B, a motion picture film 11 moves through the film inspection station and is guided around a single inspection roller 12. Possible defects which can occur are illustrated in FIG. 1B and include the following. Along an edge 11a adjacent to a sound track 14, cuts or tears which may be rather lengthy such as shown at 23 or rather short as shown at 28 can occur at the side edge and which extend into a region of the sound track 14. At the opposite side edge 11b, long and short cuts 16 and 18 may occur, and also a cut 17 which intersects a sprocket hole may occur. Also, a small notch 21 or a relatively large notch 22 which may run from the edge to the sprocket hole 15 is known to occur.

Due to mis-feed or alignment of the film, additional holes such as 19 or 20 may occur between sprocket holes. Additionally, sprocket holes may become enlarged or extended along a running direction of the film such as shown at 7 and 8.

Along a central portion 11c of the film, thickness defects such as 27 may occur. Also, film splices such as a tape splice 24 with an abutment of cut ends of the film at 25 are common. Alternatively, a so-called "cement" splice as shown at 26 may occur wherein the cut ends of the film are overlapped and glued to one another.

Although 16 mm film may be employed with the inspection station of the invention, the system is also adaptable with some modifications for other types of motion picture film such as 8 mm.

Figure 2:
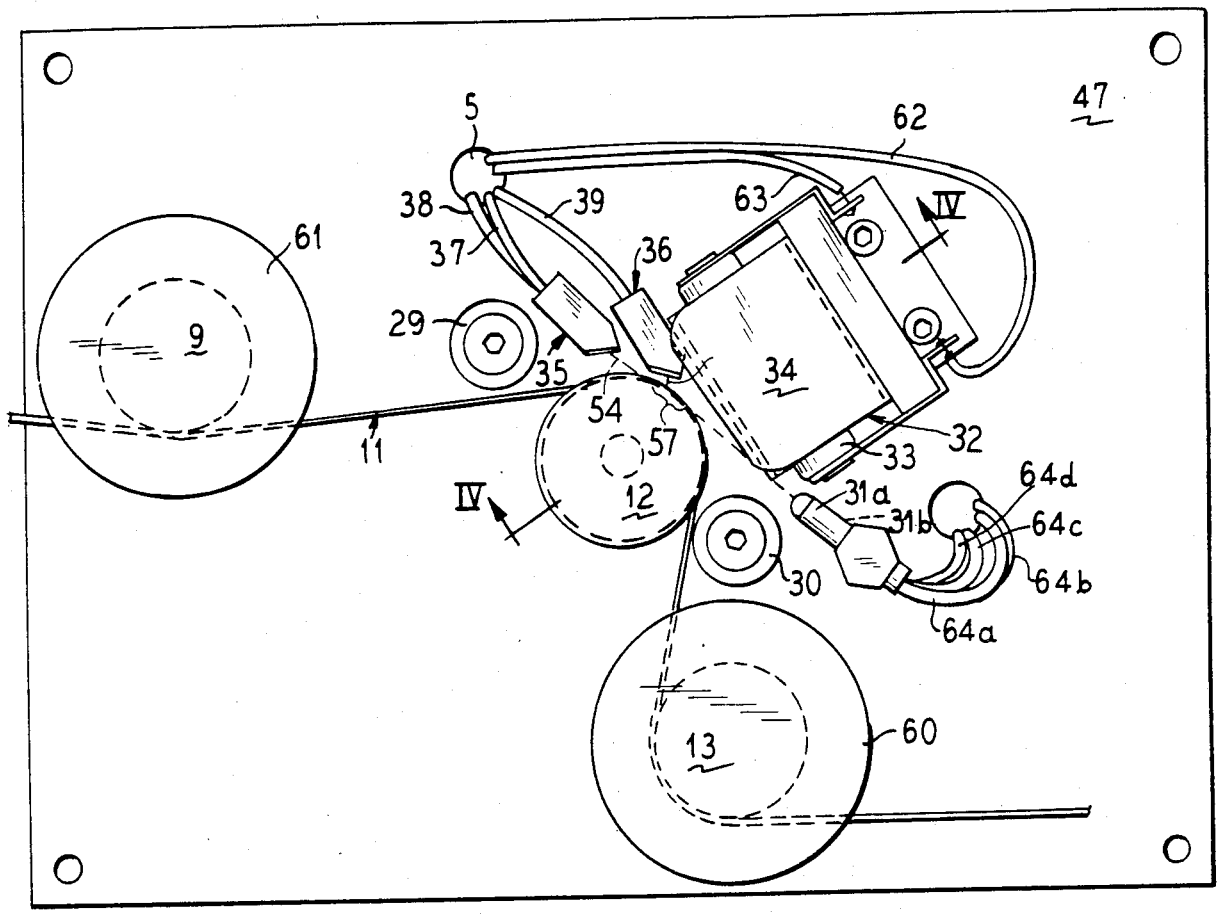
FIG. 2 is a more detailed side view of the film inspection station of a film inspection system of the invention.

As shown in FIG. 1A and also in FIG. 2, an input guide roller 9 and an output guide roller 13 are provided. Additionally, a film starting guide roller 29 and a film starting guide roller 30 are provided. The film starting rollers substantially only contact the film during start-up prior to tensioning at the rollers 9 and 13. Thereafter, the film does not touch these rollers. Thus, these rollers maintain curvature at the main inspection roller after mounting the film and permits reliable detection at start-up even though slack may not yet be out of the film.

First and second point light sources 31a and 31b are provided, preferably with Gilway lamps. These two sources lie in a plane tangent to the periphery of the inspection roller 12, and both lamps together approximately simulate a line of light. A diffused light source 32 includes a Gilway lamp 33 having a long filament which simulates a line source of light and which is surrounded by a diffuser structure 34 having diffusing reflecting walls 34a, 34b, 34c, and 34d whose interior surface is roughened and bright white.

A so-called "shadow graph" block 35 contains optics for receiving a light beam from the lamps 31a, 31b which is straight and substantially undeflected as shown at 54. The reflection block 36 contains optics for receiving a deflected light beam 55 from, lamps 31a, 31b.

A light waveguide 37 for sprocket edge side analysis is received in block 35 along with a light waveguide 38 for central film thickness analysis. A light waveguide 39 is received in block 36 for reflected light sound track edge analysis.

Referring to FIG. 1B, for sprocket hole edge analysis, the end of fiber optic 37 at 37a is spaced from a pin hole aperture 41 within a receiving hole 46 of block 35. The pin hole aperture provides a so-called "pin hole camera" effect and has a diameter of 0.040 inches.

Optical fiber 38 for sensing thickness variations along a central portion of the film is received in mounting hole 45 and has an end 38a spaced from an aperture 42 approximately ⅛ inch in diameter. The fiber optic 39 is received in hole 44 of block 36 and has an end 39a spaced from a pin hole apertrue 43 of approximately 0.040 inches diameter.

Blocks 35 and 36 are attached by mounting screws to support wall 47.

For sprocket hole analysis by a so-called "microscope real imaging", a focusing lens 48 which may have a focal length of 17 mm is aligned so that focal rays 52 focus at 57 on a periphery of the inspection roller 12 on a top surface of the film. A light shielding tube 49 which also mounts the lens 48 is provided and positioned so that the real image from focal rays 52 occurs on a plane formed by a printed circuit board 50 on which the real image 53 is projected. On the board 50, photo cells a, b, and c are spaced along a running direction of the film and such that the real image of the sprocket holes lies on the line containing the photo diodes. Printed circuit wiring 51a, 51b, and 51c serves to connect one of the electrodes of the respective diodes. The other electrode of the diodes is connected on the opposite side of the board.

The unreflected rays 54, the reflected rays 55, and the focal point of focusing rays 52 all impinge approximately at a tangent inspection region or area 57 on the film bent around the inspection roller 12.

A lower corner 56 of optical block 36 forms an upper limit for a slit through which the direct rays 54 pass, the bottom edge of the slit being formed by the inspection region 57.

The optical portion of detection will now be explained. For the sprocket side edge a "shadow graph" is formed wherein light beam 54 passing through the slit defined by 56 and 57 is substantially reduced or blocked off in intensity as a result of a partial or complete light blockage caused by free ends of a cut 16, 17, and 18 or a notch 21 or 22. Such cuts or notches cause flaring up of the cut ends because of the curvature of the film around the inspection roller, thus resulting in light blockage received through pin hole aperture 41 and focused on fiber optic end 37a. Typically, the sprocket side edge optical analysis occurs over approximately 1/16 inch wide region of a ⅝ inch wide 16 mm film. The central portion 11c approximately ⅛ inch wide is scanned by the shadow graph formed by the light beam 54 passing between slit edges 56 and 57 and received at fiber optic end 38a. Light intensity is decreased or preferably completely blocked off given an undesirable thickness of a tape splice 24, an overlapping cement splice 26, or a central defect 27 on the film of undesired thickness.

Film flaws in the form of cuts 23 or 28 along the sound track side edge are detected by a reflection principle as shown by light beam 55 deflected through pin hole aperture 43 and focused on the end 39a of the fiber optic 39.

If a tape splice such as 24 extends completely across a lateral width of the film, it is possible that all three light sensors will be affected and consequently in the electronics of the system the side edge detection is disabled given presence of a splice.

Figure 8:
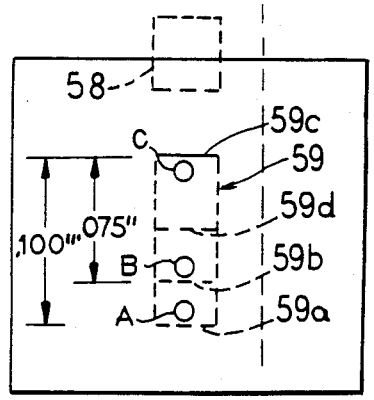
FIG. 8 is a schematic illustration for purposes of explaining sprocket hole sensing through analysis of a real image.

For analysis of sprocket holes, the real image focused on the plane containing the board 50 is projected such that when an elongated sprocket hole 59 as illustrated in FIG. 8 occurs and the edge 59c permits light reception at photodiode C, then if the sprocket hole is elongated to approximately 0.075 inches at an opposite end 59b, photo diode B will be uncovered. Conversely, if it is desired to sense an elongated sprocket hole of 0.1 inches, then the opposite edge 59a of the sprocket hole will permit photodiodes C and A to be simultaneously uncovered. Thus an elongated sprocket hole 59c-59b or 59c-59a can be detected and distinguished from a normal sprocket hole 58. The diffused light source 32 provides a white diffused light for even illumination of the area focused upon at 57. The diffused light in combination with the real image focussing concept ensures that the sprocket hole detection system will be insensitive to creases, dirt and edge lettering on the sprocket hole edge of the film.

Also with the sprocket hole inspection system of the invention, it is possible to utilize the information generated to count the total footage of the film and determine direction of travel.

With the projection system of the invention, four detection parameters are provided all appearing substantially at a single inspection region 57 by use of light beams and without the use of feeler arms so that substantially only a single relatively small inspection area or region 57 on a single inspection roller 12 results and with no use of feeler arms to cause damage to the film. At such a single location the system provides a complete analysis of the film quality.

With reference to FIG. 2 showing additional details from a side of the film inspection station of the invention, protective caps 60 and 61 over input and output rollers 9 and 13 are shown. Electrical wiring 62 and 63 for Gilway lamp 33 run through an aperture 5 in plate 47 to a circuit board 66 shown in FIG. 3. Electrical wires 64a, b, c, d connect the two Gilway lamps 31a, 31b to the circuit board 66 as shown in FIG. 3.

Figure 3:
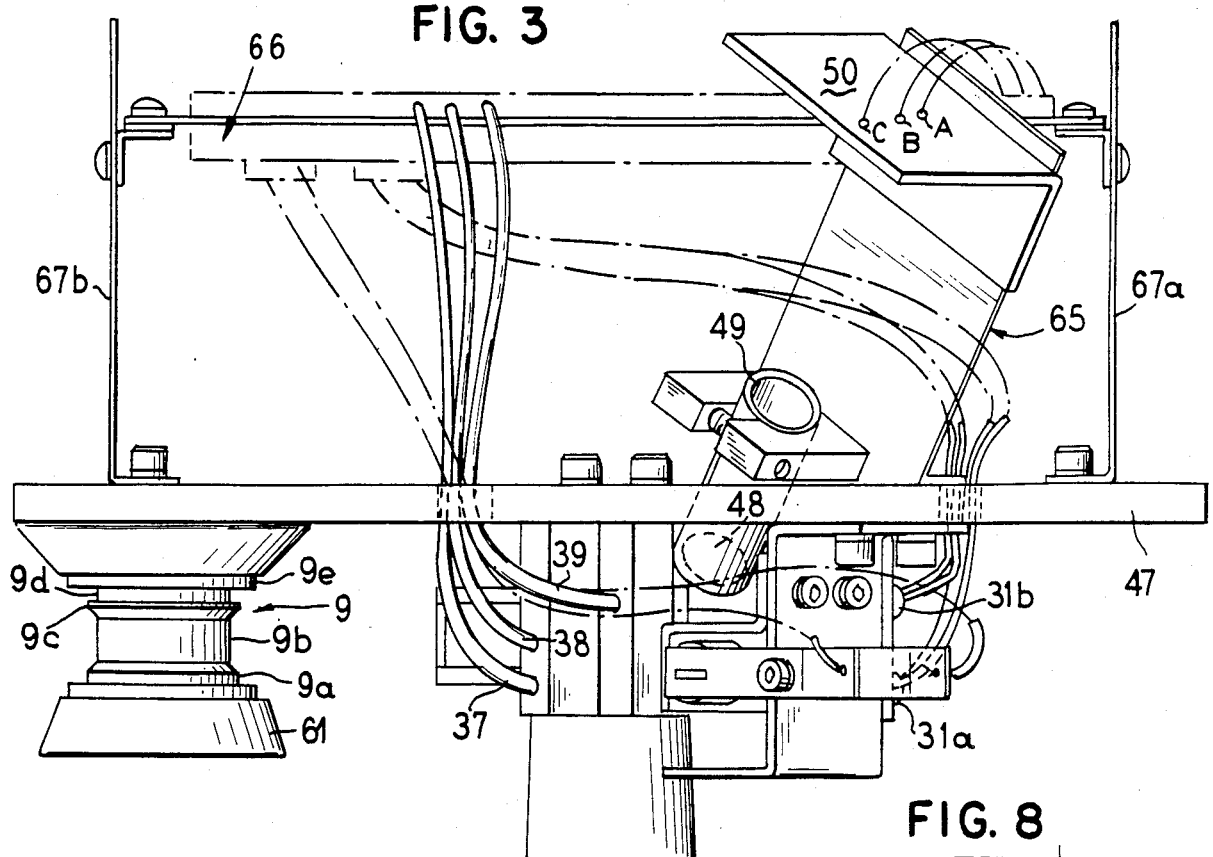
FIG. 3 is a more detailed top view of the film inspection system of the invention.

FIG. 3 clearly illustrates a mounting bracket 65 for mounting, spacing, and aligning the lens 48, protection and shielding tube 49, and board 50 lying in the real image plane. Spacer walls 67a, b also are illustrated for mounting and spacing the electronic sensing circuitry on board 66 from the film inspection station on the opposite side of mounting panel 47. Since static electricity can be generated as the film runs through the inspection station, by mounting the printed circuit board 66 on the opposite side of and at a spacing from the film inspection station, the circuitry is protected and isolated from such electrical charges (spacing of at least 1.5")

Figure 4:
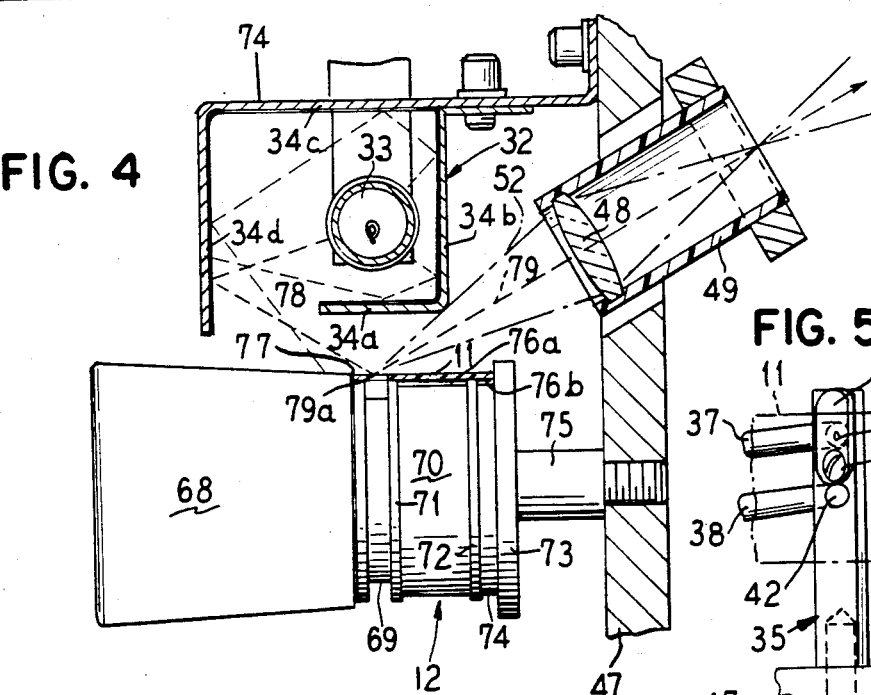
FIG. 4 is a fragmentary end view of the film inspection station showing the "real image microscope" sensing optics according to the invention.

Referring to FIG. 4, the inspection roller 12 has associated with it a tapered guide portion 68 to ease in loading or threading film to be inspected into the station. The movable roller 12 has a circular indentation or groove 69 positioned below the line of sprocket holes 77 so as to provide a void and non-reflecting surface for light beams passing through the sprocket hole. This area is preferably black. The film 11 soundtrack side edge abuts against a rim 73 and lies on circumferential projecting portions 71 and 72 so as to create gaps 76a, 76b between a bottom portion of the film and a machined down portion 70 and 74 of the roller 12. Thus, the film is supported at minimal contact points so as to prevent wear on the film surface. The roller 12 is supported on an axle 75 connected to the support wall 47.

Also to prevent wear, as shown in FIG. 3 input roller 9 has an outer film contact circular portion 9a, an inner smaller diameter portion 9b, a projecting ring 9c of similar diameter to 9a, a smaller diameter portion 9d, and a guide portion 9e for the film. The output roller 13 is designed in similar fashion.

On the roller 12, the supporting rim 72 is positioned so that a rubbing or scratching will not occur on a picture area or in a sound area of the film. Also, the smaller diameter portion 70 occurs at the central light beam projection area for film thickness measurement. The relief area under the picture area is typically 0.005 inches.

Figures 5, 6:
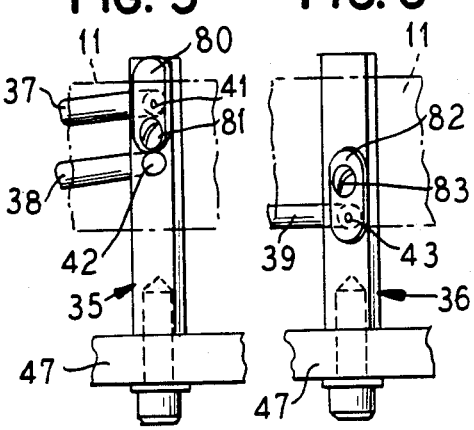
FIG. 5 is a fragmentary end view of an optical block for "shadow graph" direct beam light sensing.
FIG. 6 is a fragmentary end view of an optical block for reflective sensing.

FIG. 5 shows the "shadow graph" direct light beam receiving block 35 in an end view with the pin hole aperture 41 in a movable plate 80 mounted with screw 81 in front of sprocket hole edge side optical waveguide 37.

FIG. 6 shows a similar pin hole aperture 43 in a plate 82 attached by screw 83 to the reflector block 36 for the sound track side edge detection.

FIG. 4 exemplifies by various reflected beams 78 how diffuse light is created which reflects off the roughened white surfaces 34a, b, c, d and how such light illuminates the focal point at the sprocket hole 77 investigation area or region 79a.

The sensing or detection electronics will now be described with reference to FIGS. 7A and 7B which are continuing portions of the same schematic diagram.

The detector electronics generally shown at 84 includes sprocket hole threshold circuits 85a for reference 85b for a medium elongation of 0.075 inches, and 85c for a long elongation corresponding to 0.1 inches. Either the medium or long sprocket hole circuit is engaged with switch or jumper 133 in the sprocket hole comparator circuit 90 which connects to one input of an AND gate 134. The other input of the AND gate connects to the reference circuit 85a. The photo diodes A, B, and C are connected in the respective threshold circuits 85a, 85b, and 85c.

The sprocket hole threshold circuit 85a has its input at photo diode A. The photo diode provides a voltage to the non-inverting input of operational amplifier 110. This signal, for example, may be 0.5 volts but changes greatly such as up to 1 volt or down to 0.3 volts depending upon color of the tape, system optics, system optics including aging of the system optics or set up of system optics, dirt on the lens, light intensity, sensitivity of photo cells, diffuser or film reflectivity, the amount of contrast present at the sprocket holes, et.

Given detection of a sprocket hole, the 0.5 volt signal may go to 0.1 volts, for instance. This series of pulses corresponding to each sprocket hole is then coupled through a noise isolation resistor to the non-inverting input of amplifier 110. Amplifier 110 is a voltage gain stage whose gain is set by resistors 111 and 112. The amplified and non-inverted pulse output is connected to the inverting input of a comparator 117. The inverted signal is present at the output of the comparator and is fed back to a control input 113a of a solid state switch 113. The positive going pulse caused by the sprocket hole causes the switch to close so that through contacts 113b, 113c resistor 115 is parallel with resistor 114. Typically, the resistance 115 is many order of magnitude smaller such as ten times smaller than the resistance 114.

Thus, when sprocket holes are not present, resistor 114 will charge capacitor 116 to a given level. However, because of the closing of the solid state switch 113 with each sprocket hole on a periodic basis, and since the signal present given a sprocket hole at the output of amplifier 110 is close to ground, the voltage which would normally be on capacitor 116 is heavily weighted downwardly by the sprocket holes so that a weighted average DC signal with a small ripple is present on capacitor 116. This weighted average voltage across capacitor 116 is applied to the non-inverting input of comparator 117 and serves as a floating tracking reference which automatically tracks overall system parameter changes and external environmental influences as previously described. An advantage of the circuit is that it does not have to be "set up" but rather automatically adjusts to conditions present.

Voltage amplifier 110 may constitute IC LM 24 and comparator 117 may constitute IC LM 339. The solid state switch may constitute IC 4016.

The AND gate 134 output is activated when both the reference and either one of the long or medium threshold circuits provides a pulse output so as to cause a pulse output amplified through amplifier 95 to activate an enlarged sprocket hole indicator 96 which may be a light or other indicator for an operator of the machine.

The sprocket side edge threshold circuit 86 receives light from fiber optic 37 which is translated into a voltage at the output of photo diode 119. Unlike the sprocket hole system previously described, film defects are not constantly occurring and thus the signal present at the non-inverting input of operational amplifier 125 has substantially a DC voltage without substantial pulsing when defects are not present. At its inverting input operational amplifier 125 has resistors 123 and 124 connected so as to set a voltage gain of this voltage amplifier. FET 126 connected at the output with its gate also connected to ground functions as a constant current source so as to include ground reference in the output of the amplifier 125.

The non-inverted but amplified DC level of the output of amplifier 125 is fed to the inverting input of a comparator 130. Resistor 127 connected to the output of amplifier 125 and capacitor 128 form a circuit for providing an average DC value of the input signal. Sensitivity potentiometer 129 then samples this DC value and provides a set point at the non-inverting input provided in the film at the splice location, i.e. through the splice overlap or through the splice tape. This constitutes an acceptable splice.

Case "two" shows an unacceptable splice in which the sprocket holes are not present in the splice area and have not been punched through the splice tape, for example.

Case "three" shows a shorter splice such as an overlap "cement" splice wherein the sprocket hole has been punched at the overlap location. Case "four" again shows a defective splice since a sprocket hole is missing during the splice, such as in an overlap splice.

Figure 9A:
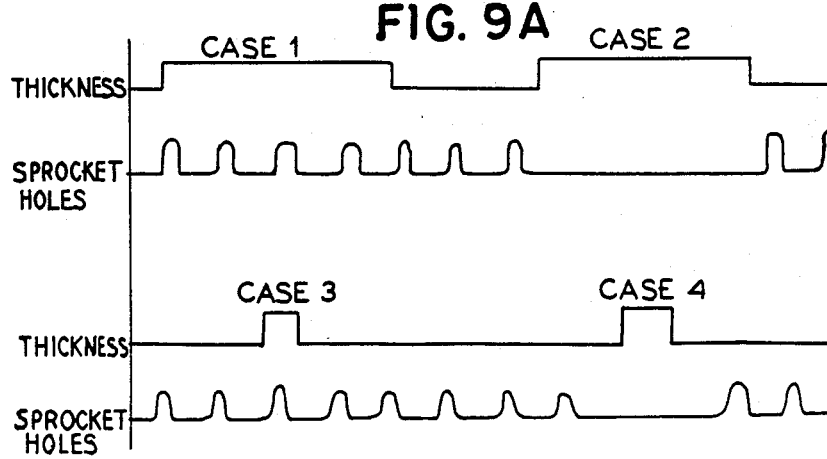
FIG. 9A shows comparative wave forms and FIG. 9B a circuit in an additional embodiment of the invention for analyzing whether a splice has sprocket holes.
Figure 9B:
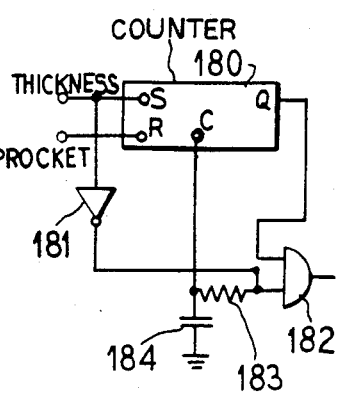

The circuit in FIG. 9B comprises a counter 180 with the thickness signal provided to the set input S and a sprocket signal provided to the reset input R. A clear input C receives the signal through the inverter 181 from the thickness input, then through a time delay circuit resistor 183 and capacitor 184. The Q output of the counter connects to one input of an AND gate 182 whose other input connects to the inverter 181. The output will indicate the defective splices for case "two" and case "four".

Figure 10:
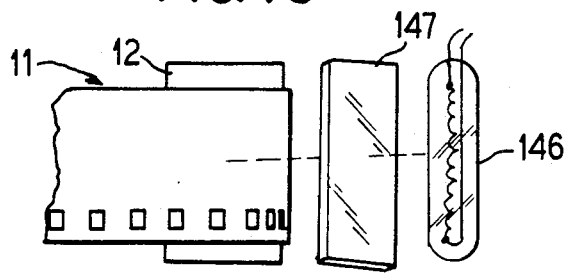
FIG. 10 is an alternate embodiment of the invention for diffusing light in connection with the "real image" optical analysis system for sprocket holes.

FIG. 10 is an alternate embodiment for diffusing light in connection with the real image "microscope" sprocket hole optical analysis system. In place of the multi-walled light diffusing enclosure 34, a light diffusing and light transmissive roughened glass plate 47 is provided between the light source 146 and the tape 11 at the area desired to be eliminated.

FIGS. 11A, 11B, and 12 show an alternate method and apparatus for determining defects at a sprocket hole side edge of the film. In the previously described side edge detection systems, at the sound track side edge it is desirable to detect for cuts at least 0.070-0.075 inches inboard of the edge in order to avoid detecting numerous very small edge cuts right at the edge and which do not constitute a sufficient defect in the film to stop the machine and inform the operator. On the sprocket hole side edge of the film, however, since the sprocket holes are set inboard typically 0.030 inches, it is thus impossible to set the side edge cut detecting system as far as desired. Consequently, rather than using the reflecting method which picks up the numerous small minute cuts directly at the edges, as previously described the shadow graph technique is employed which can be aligned to detect between the sprocket hole and the edge of the film and which can be set through use of the pin hole aperture so as to avoid detecting the numerous small cuts directly at the edge. However, a disadvantage of the shadow graph is that it has a longer set-up time whereas the reflecting sensing system can be set up in a shorter period of time.

In order to avoid both of the above difficulties, as shown in FIG. 11A a first optical waveguide 153 is aligned in a first hole 156, and is aligned so as to receive light 205 reflected off the film between the sprocket holes and the edge of the film. A pin hole aperture at 160 of 0.030-0.040 diameter is also employed. A second fiber optic 154 is aligned in a hole 155 and second pin hole 161 of diameter 0.030-0.040, diameter is provided so as to focus light on the end of the fiber optic 154. This fiber optic is aligned to receive reflected light 206 along the line of the sprocket holes. The angle of inclination is generally shown in FIG. 11B. The same light sources as previously described, namely Gilway lamps 31a and 31b are employed for sending the light beams for the reflection. Pin hole aperture plates 158 and 210 may be mounted with screws 159 and 211 as shown in FIG. 11A.

The optical block 148 which is mounted to the support surface 47 via a screw aperture 162, also has the sound track fiber optic 39 operating on the reflection principle and having the pin hole aperture 43 also 0.040 inches in diameter. Thus, the block 148 replaces the previously described reflector block 36.

Figure 7A:
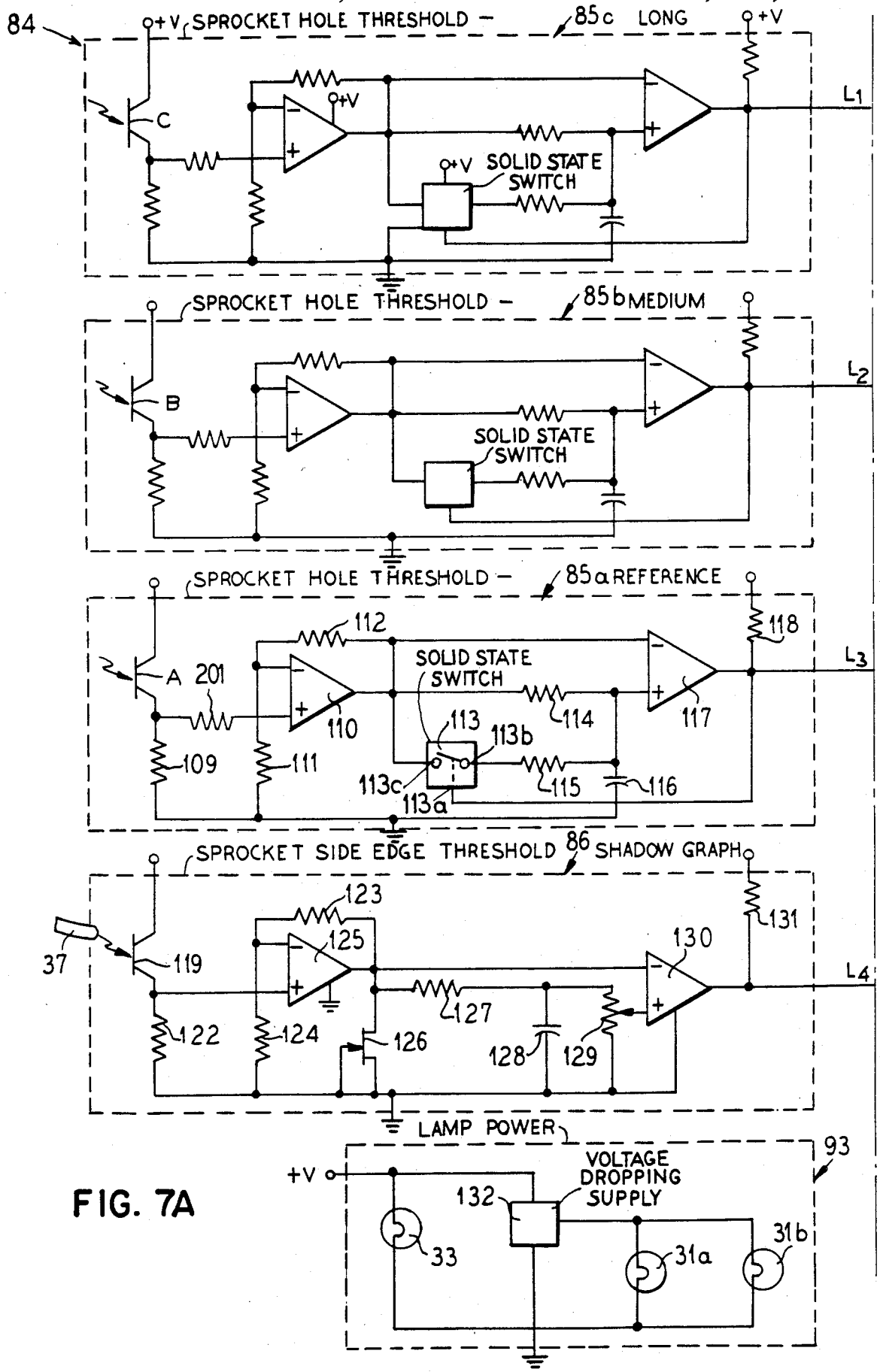
FIGS. 7A and 7B are a schematic diagram of sensing electronics for use with the film inspection station previously described.
Figure 7B:
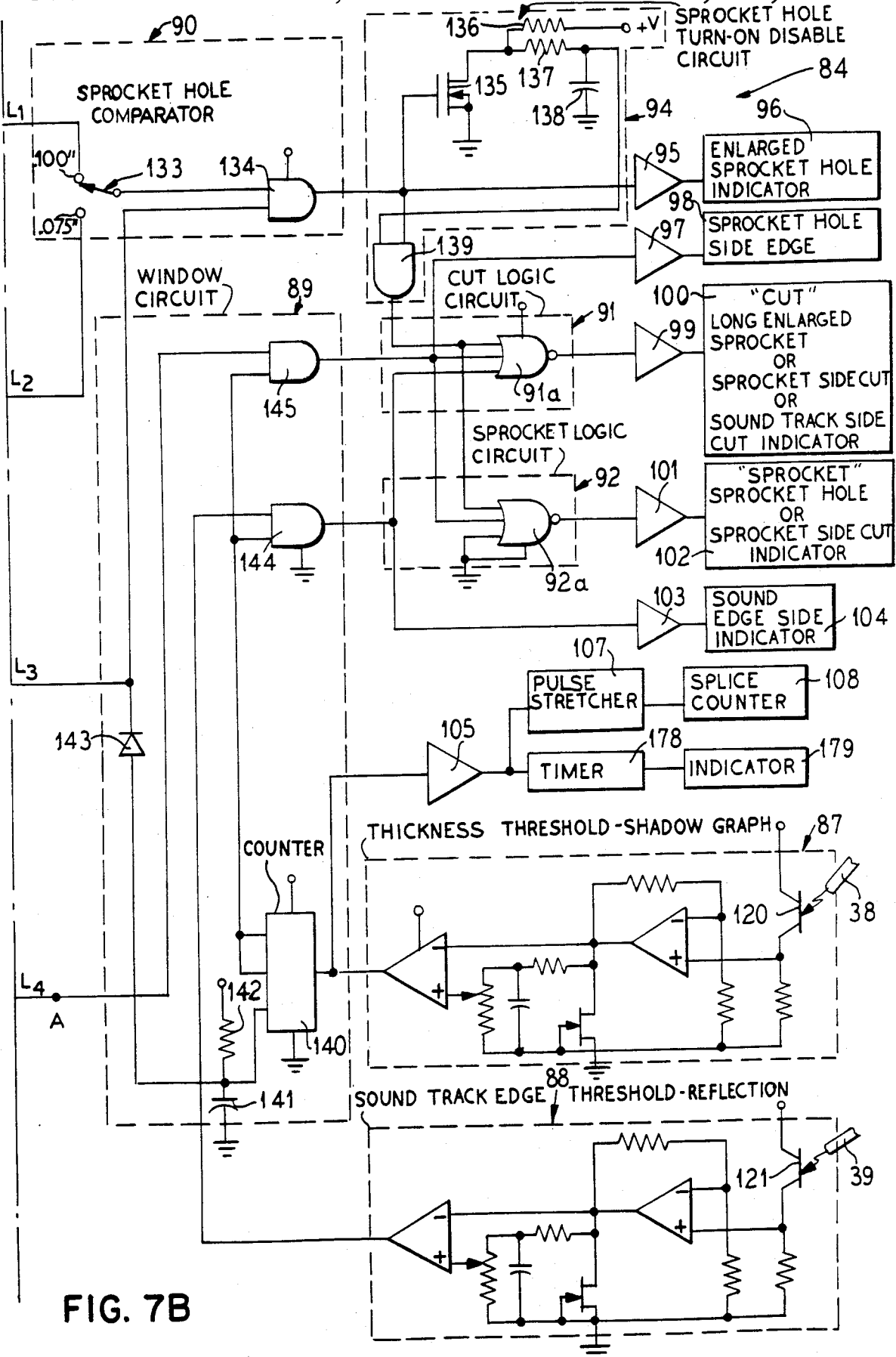

In place of the previously described sprocket side edge threshold shadow graph system the electronics shown in FIG. 12 is employed and connects at point A in FIGS. 7A and 7B. As previously described for the sprocket side edge threshold circuit 86, the threshold circuit has a photo diode 166, ampifier 170, comparator 176, set-up pot 175, capacitor 174 with resistor 172, FET 173, gain setting 169 and 171, input resistor 168, and output resistor 177. The spocket hole threshold-reflection circuit 163 and the sprocket side edge threshold circuit 164 of similar construction connect through an AND gate 165 to point A.

The above system operates as follows. Since the reflective principle is employed, set-up time is reduced for both optical receivers and associated electronics. If the reflective edge sensor optics 153 picks up a small cut 151 between sprocket holes, then no signal will be emitted and the AND gate 165 and the small cut 151 will not be indicated as a flaw. If a small or large cut 150 occurs lateral to a sprocket hole, then signals will be emitted by both threshold circuits and an output will occur at the AND gate. Thus, a cut, even if small and directly opposite a sprocket hole, will be indicated as a defect. If a large cut 149 occurs which extends inboard of the film edge and between sprocket holes, then both detectors will register a signal and the AND gate will indicate a defect. Thus, detection of small cuts 151 between sprocket holes is avoided while still employing the reflective technique which permits rapid set-up.

Although various minor changes and modifications might be proposed by those skilled in the art, it will be understood that we wish to include within the claims of the patent warranted hereon all such changes and modifications as reasonably come within our contribution to the art.

We claim as our invention:

1. A system for determining defective edge cuts at a sprocket hole side of a motion picture film while avoiding detection of cuts which do not constitute a film defect at said side edge, comprising:

an inspection roller;
means for guiding said motion picture film over a curved portion of said inspection roller;
at an inspection region of said film at a periphery of the inspection roller, at one side of said inspection region a light source and at an opposite side thereof first and second light receivers positioned so as to receive reflected light from said inspection region;
the first light receiver being aligned to receive reflected light between a sprocket hole side edge of the film and an edge of the sprocket holes adjacent said sprocket hole side edge;
the second light receiver being positioned to receive reflected light from said inspection region at the sprocket holes;
first and second circuit means respectively connected to the first and second light receivers for respectively providing a first signal when the first light receiver senses cuts and for providing a second of comparator 130. This set point may be, for example, between 10% and 90% of the average DC value. When set to 10%, when a defect is present causing an absence of light resulting in a drop of the voltage close to ground at the output amplifier 125, then the comparator 130 will only sense a relatively serious defect since in order to provide an output the signal at the inverting input of comparator 130 must also be close to ground which represents a relatively complete blockage of light at the photo diode. For greater defect sensitivity, for example, 90% could be chosen as the setting at potentiometer 129. Typically a 50% setting will result in a system which is insensitive to minor flaws yet will trigger a system given major flaws.

Threshold circuits 87 and 88 are similar to 86 although the gain of the input amplifier 125 may be set to different values to handle different signal levels.

As previously explained with respect to threshold circuit 85a for sprocket holes, an automatic tracking of floating reference is thus provided so as to automatically compensate for the variables previously discussed in connection with circuit 85a.

The operation of the thickness threshold circuit - shadow graph 87 and sound track edge threshold circuit - reflection 88 are similar to 86.

A power supply 93 for the Gilway lamps 33, 31a, 31b is provided and includes a voltage dropping power supply 132 formed by IC 7805.

The thickness threshold circuit 87 outputs through amplifier 105 to an adjustable timer 178 adjusted for running speed and which indicates when a splice is longer than a given time length and thus defective. The indicator will light a light or give some other indication to the inspection station operator.

The pulse stretcher 107 receiving a pulse from amplifier 105 stretches the given pulse to 50 ms so as to provide an effective pulse for operating a splice counter 108 which can be set to count total splices on a given film being analyzed.

A window circuit 89 receives as inputs pulses from the sprocket hole threshold reference circuit, sprocket side edge threshold circuit, sound track edge threshold circuit, and thickness threshold circuit. A counter 140 comprising circuit type 4D22 receives as an input the pulses from the thickness threshold circuit 87 and outputs to AND gate 144 and AND gate 145. A sprocket hole pulse is also input through isolating diode 143 and through a series noise take-out circuit formed of resistor 142 and capacitor 141 and is input to the counter 140.

The counter counts a predetermined number of sprocket holes such as 1 through 8, and preferably 3, and then provides an enable signal to turn both the sprocket hole side edge channel and sound track side edge channel on through AND gates 144 and 145. Also, if the thickness pulse is received, the counter will turn off both edge channels via AND gates 144 and 145.

The edge channels are turned off where a thickness indicative of a splice is received since typically the splice will extend across a whole width of the film and it is not desired that the edge channels provide an output since they are intended to provide an output only indicative of cuts rather than a splice. They are turned on after a predetermined count such as three sprocket holes so as to resume their normal functioning at the time when it is known that the splice has passed since typically most splices will not extend for a total time period represented by a length of film corresponding to three sprocket holes. Thus, an "OFF" window is provided for the system given a splice detection.

A so-called cut logic circuit 91 combines outputs from the sprocket hole comparator indicative of a longitudinally enlarged sprocket hole, from the sprocket side edge cut threshold circuit, and from the sound track edge cut threshold circuit. The system will thus provide an output to amplifier 99 when at least any one of the above outputs is received. A NOR gate 91a receives these three inputs (IC type 14025) and, given the presence of any one of the above three signals, provides an output through amplifier 99 to a "cut" indicator 100 which lights a lamp or provides some other indicator to the operator that either a longitudinally enlarged sprocket hole, sprocket hole edge cut, or sound track edge cut has been encountered and, if desired, stop the machine.

Similarly, a sprocket logic circuit 92 containing a NOR gate 92a receives an input indicative of a longitudinally enlarged sprocket hole or an edge cut at the sprocket hole side and in either event outputs through amplifier 101 to a "sprocket" indicator 102 of either a longitudinally enlarged sprocket hole or sprocket hole side cut and provides an indicator to the operator and/or stops the machine.

Individual outputs are also provided at amplifier 95 and indicator 96 for a longitudinally enlarged sprocket hole, at 97, 98 indicative of a sprocket hole side edge cut, and at 103, 104 indicative of a sound side edge cut. In these cases the machine may be stopped and the operator informed by the indicator of such defects.

A sprocket hole turn-on disable circuit 94 contains an FET 135 whose gate connects to the output of the sprocket hole comparator circuit 90. The source-drain path is provided with voltage through resistor 136 and outputs through resistor 137 and capacitor 138 at ground a signal enabling the cut logic circuit 91 and sprocket logic circuit 92, dependent upon an initial turn-on time delay set by resistor 137 and capacitor 138 such as for two or three sprocket holes when the film first begins to run through the inspection station. This is provided because the initial pulse train indicative of defective sprocket holes from the sprocket hole comparator 90 must be inhibited from reaching a cut logic circuit 91 and sprocket logic circuit 92 since at initial start-up the system is at low light sensitivity and may be responding to room light. When the film has been threaded and the machine turned on the sixty-cycle flicker of ambient room light can cause signals from all three photo cells A, B, and C resulting in a faulty sprocket hole comparator output. This problem is present at least during initial turn-on as the film comes up to speed for the first three sprocket holes. This problem is caused by ambient room light occurs since the threshold circuit automatically adjust via the auto tracking reference to a relatively high sensitive operating condition since light has not yet been received by the three photo cells from the Gilway points or lamps. After the system is running for a short period, however, the threshold circuits readjust themselves so that room light does not trigger the threshold circuits.

FIGS. 9A and FIG. 9B show an additional feature of the system wherein the "thickness" output from threshold circuit 87 and sprocket hole output from threshold-reference circuit 85a are combined to determine whether or not a proper splice has been made. In case "one", the first line of the graph indicates a typical splice wherein sprocket holes have been successfully signal when said second light receiver detects sprocket holes or cuts; and output circuit means connected to said first and second circuit means for providing an output signal only when both of said first and second signals are present, whereby edge cuts which do not extend to a line containing outer side edges of the sprocket holes and which are also between sprocket holes do not trigger said output signal.

2. A station according to claim 1 wherein the optical detection means includes at least one fiber optics and means for positioning a pin hole aperture at a distance from a cut end of the fiber optics so as to focus a real image thereat.

3. The system according to claim 1 wherein the first and second receivers each have pin hole apertures which provide the projection of a real image onto a cut end of the fiber optics.

4. The system according to claim 1 wherein the first and second circuit means include means for providing an automatic tracking reference comprising a substantially DC voltage based upon an average of a composite signal from the first and second light receivers.

5. A system for determining significant defective edge cuts at a sprocket hole side of a motion picture film while avoiding detection of less significant cuts at said edge, comprising:

an inspection region and film support means at said inspection region;

a light source radiating at said inspection region;

a sprocket hole light receiver means for scanning a sprocket hole portion of said film at said inspection region;

sprocket hole side edge light receiver means for scanning between the sprocket holes and the sprocket hole side edge; and comparator means for comparing outputs from both of said receiver means so as to not provide a signal output when a defect at said sprocket side edge of the film does not extend inboard as far as the sprocket holes and also lies between the sprocket holes.

6. A system according to claim 5 wherein a thickness detector means is provided for providing an output signal as long as a splice on the film is being scanned; and comparison means connected to said thickness detector means and sprocket hole light receiver means for providing a signal when sprocket holes are not present during a time when the splice output signal is present.

7. A film thickness detection system for determining whether a splice in a motion picture film has been properly punched with sprocket holes at a location of the splice, comprising:

first optical sensing means for providing a pulse signal having a time duration indicative of a length of the splice along a running direction of the film;

second optical sensing means for providing a signal pulse corresponding to each sprocket hole on the film; and comparison means connected to said first and second optical sensing means for providing a signal indicative of when sprocket hole signals are not received during said time duration of the splice pulse.

8. A system according to claim 7 wherein said first optical sensing means comprises an optical detector wherein a splice providing additional thickness to the film blocks out a portion of a light beam.

9. A system according to claim 8 wherein the second optical sensing means comprises an optical unit for receiving a reflection of a light beam aimed at a sprocket hole on the film.

10. A system according to claim 8 wherein said second optical sensing means comprises means for creating a real image on a projection plane of the sprocket holes at an inspection region.

* * * * *